United States Patent
Kropf

(10) Patent No.: US 9,561,112 B2
(45) Date of Patent: Feb. 7, 2017

(54) JOINT ENDOPROSTHESIS AND METHOD FOR ASSEMBLING SUCH A PROSTHESIS

(75) Inventor: Philipp Kropf, Cham (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 1306 days.

(21) Appl. No.: 12/096,839

(22) PCT Filed: Mar. 12, 2007

(86) PCT No.: PCT/CH2007/000134
§ 371 (c)(1),
(2), (4) Date: Aug. 21, 2008

(87) PCT Pub. No.: WO2007/131369
PCT Pub. Date: Nov. 22, 2007

(65) Prior Publication Data
US 2009/0018664 A1    Jan. 15, 2009

(30) Foreign Application Priority Data
May 12, 2006 (EP) ................................. 06009804

(51) Int. Cl.
*A61F 2/40* (2006.01)
*A61B 17/86* (2006.01)
(Continued)

(52) U.S. Cl.
CPC .............. *A61F 2/4081* (2013.01); *A61B 17/86* (2013.01); *A61F 2/34* (2013.01); *A61F 2/4637* (2013.01); *A61F 2002/305* (2013.01); *A61F 2002/30331* (2013.01); *A61F 2002/30354* (2013.01); *A61F 2002/30485* (2013.01); *A61F 2002/30487* (2013.01); *A61F 2002/30604* (2013.01); *A61F 2002/30808* (2013.01); *A61F 2002/30822* (2013.01); *A61F 2002/30878* (2013.01);
(Continued)

(58) Field of Classification Search
CPC .................... A61F 2002/30878; A61F 2/4081; A61F 2002/30332; A61F 2220/0025; A61F 2002/30112; A61F 2002/30235; A61F 2002/30433; A61F 2002/30507; A61F 2002/30726; A61F 2/40; A61F 2/4059; A61F 2/30749; A61F 2002/305; A61F 2/4003
USPC ............................................ 623/19.11–19.14
See application file for complete search history.

(56) References Cited

U.S. PATENT DOCUMENTS 5,032,132 A * 7/1991 Matsen et al. ............ 623/19.11
5,702,447 A   12/1997 Walch et al.
(Continued)

FOREIGN PATENT DOCUMENTS

EP  0664108    7/1995
EP  1472999   11/2004
(Continued)

*Primary Examiner* — Ann Schillinger
(74) *Attorney, Agent, or Firm* — Fay Kaplun & Marcin, LLP

(57) ABSTRACT

A prosthesis, in particular a shoulder prosthesis, includes a socket part receiving a joint head; an anchoring part anchoring the prosthesis in a bone; and a connecting arrangement securely connecting the socket part to the anchoring part. The socket part is assigned at least one pin and the anchoring part has at least one guide. The guide is designed in such a way that the pin can be held substantially safe from tilting in the guide.

27 Claims, 2 Drawing Sheets

(51) Int. Cl.
    *A61F 2/34*          (2006.01)
    *A61F 2/46*          (2006.01)
    *A61F 2/30*          (2006.01)

(52) U.S. Cl.
    CPC ............ *A61F 2002/30892* (2013.01); *A61F 2002/30901* (2013.01); *A61F 2220/0025* (2013.01); *A61F 2220/0033* (2013.01); *A61F 2310/00011* (2013.01)

(56) References Cited

U.S. PATENT DOCUMENTS

| | | | |
|---|---|---|---|
| 6,228,119 B1 * | 5/2001 | Ondrla et al. | 623/19.11 |
| 6,679,916 B1 * | 1/2004 | Frankle et al. | 623/19.12 |
| 7,169,184 B2 * | 1/2007 | Dalla Pria | 623/19.12 |
| 7,922,769 B2 * | 4/2011 | Deffenbaugh et al. | 623/19.11 |
| 2003/0055507 A1 * | 3/2003 | McDevitt et al. | 623/19.11 |
| 2004/0064189 A1 | 4/2004 | Maroney et al. | |
| 2006/0069443 A1 | 3/2006 | Deffenbaugh et al. | |
| 2010/0070044 A1 | 3/2010 | Maroney et al. | |

FOREIGN PATENT DOCUMENTS

| | | |
|---|---|---|
| EP | 1639967 | 3/2006 |
| GB | 2405346 | 3/2005 |
| JP | 2000-005205 | 1/2000 |
| JP | 2004-113803 | 4/2004 |
| WO | 2005020858 | 3/2005 |

\* cited by examiner

JOINT ENDOPROSTHESIS AND METHOD FOR ASSEMBLING SUCH A PROSTHESIS

FIELD OF INVENTION

The invention concerns a prosthesis, in particular a shoulder prosthesis, with a socket part to receive a joint head, an anchoring part to anchor the prosthesis to a bone and a connecting device for a secure connection of the socket part with the anchoring part. The invention also concerns a method for assembling such prosthesis.

Prostheses of this kind are commonly employed for ball and socket joints, especially in shoulder and hip joints. In a shoulder joint such prosthesis forms a glenoid element to receive the head of a humerus.

BACKGROUND INFORMATION

The U.S. Pat. No. 5,702,447 A discloses a glenoid prosthesis having a planar metal socket for threading into a shoulder-blade bone. The metal socket is fitted on its inner side with a rib. A pan-like plastic socket part can be partly inserted in an oblique position under the rib, and then securely joined with the metal socket by pushing it down. The exact positioning of the plastic socket part in the metal socket demands a high precision. Any substance between the plastic socket part and the metal socket, such as for instance blood or tissue portions, may hinder a completion of the connection. Thanks to a simple tilting motion, the plastic socket part can be released from the metal socket, and the prosthesis is no longer operable. The two components of the prosthesis, the plastic socket part and the metal socket, are then totally detached from each other and cannot be securely recombined by a simple operation.

The patent application US 2004/0064189 A1 disclosed a glenoid element with an anchoring part to be anchored in a bone by a screw, and a socket part connected to the anchoring part by a snap-in device set in its bottom. When assembling the socket part with the anchoring part, however, the socket part may cant or tilt over in the anchoring part, thus impeding a secure connection of the two parts, and demanding a high precision. Moreover, any portions of tissue and blood eventually lodging between the socket part and the anchoring part aggravate a secure connection.

SUMMARY OF INVENTION

The present invention relates to a prosthesis which includes a socket part, an anchoring part and a connecting arrangement. The socket part include at least one pin and the anchoring part includes at least one guide. The guiding action is configured so as to enable the pin to be held or held in the guide in an essentially tilt-proof manner. By such a configuration of the guide, the pin may be inserted into the guide and guided or held in the same. This ensures a durable connection between the socket part and the anchoring part. Should the connecting device fall open and the socket part be detached from the anchoring part, a falling apart of the prosthesis would still not ensue, because the pin assigned to the socket part would remain inside the anchoring part guide.

The expression "essentially tilt-proof" in this context also embraces situations wherein the pin is tilted in its guide up to 10 degrees, preferably up to one degree at most, relative to the guiding axis.

In a preferred example of embodiment of the invention, the guide and the pin are configured in an essentially cylindrical manner, where the inner diameter of the guide essentially corresponds to the outer diameter of the pin, so that when inserting the pin into the guide, the outer surface of the pin slides along the inner surface of the guide. The pin can thus be guided through and held in the guide in a particularly tilt-proof manner. Substances such as for instance blood can also be prevented from depositing on the pin or on the guide.

The expression "essentially cylindrical" in this context comprises configurations with a cone up to 10 degrees, preferably up to one degree at most. Fine grooves or channels in the cylinder surface are possible.

In another example of embodiment of the invention, the connecting device for securely connecting the socket part with the anchoring part is realized as a snap-in device. A secure connection is in this case understood to be a connection requiring an applied force of at least 20 kp (196.13 Newton) to come unhitched. A first portion of the connecting device is preferably set on the pin at a distance from the socket part, and a second portion of the connecting device is set on the guide at a distance from an inserting end of the guide. The pin can be introduced into the inserting end of the guide. The distancing of the first and second portion of the connecting device can ensure that the pin is led through the guide in a tilt-proof manner, before a secure connection between the socket part and the anchoring part is established by the connecting device. The distancing further ensures that upon opening of the connecting device the pin cannot be simply loosened from the guide, but remains held in the same. A renewed connection between the socket part and the anchoring part can be achieved by simply exerting a push on the anchoring part, so as to impel the pin into the guide to such a depth as to allow the first element to cooperate with the second element and thus accomplish a secure connection between the socket part and the anchoring part.

According to a further preferred example of embodiment, the distance from the socket part of the connecting device, especially to the socket part's opposite extremity, is between 3 millimeter and 12 millimeters, in particular 4 millimeters. These distances allow achieving a particularly safe guidance and support of the pin through the guide, even if the connecting device opens, without extending the guide to such a length as to require deep boreholes or incisions for anchoring the prosthesis to a bone. Also, only a small force need be applied for securely connecting the socket part to the anchoring part, as the necessary force is in particular in the range between 15 kp and 22 kp (147.10 Newton to 215.75 Newton). The force needed to undo the secure connection between the socket part and the anchoring part amounts to at least 20 kp (196.13 Newton). The requisites regarding an extracting force are thus fulfilled.

According to an additional example of embodiment of the invention, the first portion of the connecting device to be provided on the pin is conformed as an opening, preferably an essentially annular groove. The second portion of the connecting device is preferably configured as a thickening, in particular as an essentially ring-shaped bulge. This allows a secure connection between the socket part and the anchoring part to be achieved over the shaft and the guide, by locking or snapping the thickening or bulge into the opening or into the groove. The opening is preferably fitted at its rim with a chamfer, so that inserting the pin into the guide will not cause any or only a minor shearing of the pin due to the thickening or to the second portion of the connecting device.

According to another preferred embodiment of the invention, the guide has an internal diameter of between 3 millimeters and 9 millimeters, in particular 7 millimeters.

This choice of an internal diameter allows only a small force to be applied for securely connecting the socket part to the anchoring part, where the required force runs in particular from 15 kp to 22 kp (147.10 Newton to 215.75 Newton), while the minimum force to release the secure connection between the socket part and the anchoring part is at least 20 kp (196.13 Newton), thus fulfilling the requisites.

According to a further preferred embodiment of the invention, the guide has an outlet opening on the side turned away from the entering side. This outlet opening advantageously allows any substances contained in the guide, such as for instance elements of tissue or blood to flow out, so that an unimpeded introduction and an unimpeded support of the pin in the guide, as well as an unimpeded secure connection of the socket part with the anchoring part may occur.

A fastening device, in particular a screw, may be provided in the outlet opening to fasten the anchoring part in a bone. In addition to a fastening action, where the anchoring part is for instance beaten into a bone by a hammer, the fastening device can in itself achieve a better support.

According to another preferred embodiment of the invention, the anchoring part has a bearing surface fitted with an opening to insert the pin into the guide. The opening to introduce the pin preferably forms the entering side of the guide. The bearing surface is preferably conformed so that the socket part can be applied to the bearing surface in a planar manner. At the connecting or coupling point, the curving radii of the socket part and of the bearing surface are preferably the same, thus allowing it to achieve a good resting contact. The bearing surface offers additional support for the socket part and protects the guide from intruding substances such as elements of tissues and blood. The planar application impedes a sliding or "shaking" of the socket part on the bearing surface to the widest possible extent.

According to a further preferred embodiment of the invention, the distance from the bearing surface to the connecting device amounts to between 3 millimeters and 12 millimeters, in particular 4 millimeters. This distance essentially corresponds to the mentioned preferred distance between the socket part and the first portion of the connecting device. Thank to the chosen distance, a safe guidance and a safe support of the pin within the guide itself is ensured. Moreover, the forces to be applied for securely connecting the socket part to the anchoring part can be minimized, while maintaining or exceeding the force needed to release the secure connection.

According to an additional preferred embodiment of the invention, several pins are assigned to the socket part, and the anchoring part has several guides for a tilt-proof guidance of the pins. The number of guides preferably corresponds to the number of the pins. Preferably, two to three pins and two to three guides are provided. In an especially preferred manner, the socket part is assigned two pins, and the anchoring part has two guides. The pins and the guides are preferably oriented in parallel to each other. A provision for several pins and guides can prevent a twisting of the socket part with respect to the anchoring part. The rotational stability of the prosthesis is thus enhanced.

The method for assembling a prosthesis of the above-mentioned type according to the invention is characterized in that at least one pin is inserted in the at least one guide of the anchoring part, until a secure connection between the socket part and the anchoring part is established by the connecting device. In case of an opening-up of the connecting device, this can prevent the socket part from losing effective contact with the anchoring part, because the pin assigned to the socket part continues to be held in the anchoring part's guide.

According to a preferred embodiment of the method according to the invention, in order to form a secure connection between the socket part and the anchoring part, a first element set up on the pin snaps into a second element set up on the guide of the connecting device. A particularly secure connection between the socket part and the anchoring part can thus be achieved.

BRIEF DESCRIPTION OF THE DRAWINGS

Additional advantageous configurations of the invention derive from the subordinate claims and examples of embodiment illustrated with the aid of the drawings, which show:

In these figures, the same reference symbols designate elements with a structurally or functionally identical action.

DETAILED DESCRIPTION

Figure 1:
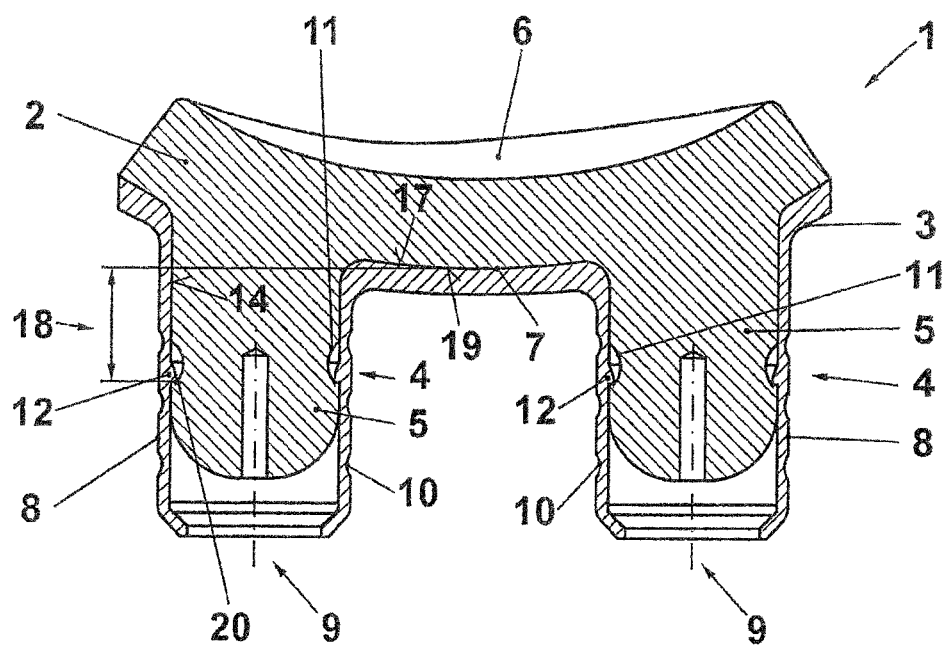
FIG. 1: a cross-sectional representation of a preferred example of embodiment of a prosthesis according to the invention.

FIG. 1 illustrates a cross-sectional representation of a preferred example of embodiment of a prosthesis 1 according to the invention. The prosthesis 1 can in particular be implanted in the portion of a shoulder blade that serves to receive a humerus head. In particular, this therefore concerns a glenoid prosthesis. The prosthesis 1 can of course also be implanted in a hip joint to receive a femur head.

The prosthesis 1 comprises a socket part 2 to receive a joint head and an anchoring part 3 to anchor the prosthesis 1 in a bone. A connecting device 4 is provided to securely connect the socket part 2 with the anchoring part 3. The socket part 2 is assigned two pins 5, where the socket part 2 and the pins are preferably executed in a single piece. An intrusion of dirt between the pins 5 and the socket part 2 can thus be prevented. The socket part 2 and/or the pins 5 are preferably made of a plastic material, especially of polyethylene. The anchoring part 3 is preferably made of a metal.

It is also possible to provide only one pin 5 or more than two pins 5, especially three pins 5. An application of more than one pin 5 has the advantage that the rotational stability of the connection of the socket part and anchoring part is high. The pins 5 are preferably arranged around the centre of the socket part in a symmetrical manner. The socket part 2 has a pan 6 to receive a joint head, and the pins 5 are arranged on the side 7 of the socket part 2 opposite the pan 6.

The anchoring part 3 has two guides 8 conformed to enable the pins 5 to be held in the guides 8 in an essentially tilt-proof manner. If more or less than two pins 5 are provided, the number o guides 8 corresponds to the number of the pins 5. The pins 5 and the guides 8 are arranged in a manner parallel to each other and essentially conformed in a cylindrical shape, where the inner diameter of the guides 8 essentially corresponds to the outer diameter of the pins 5, so that a safe support of the pins 5 in the guides 8 is established. Moreover, an intrusion of dirt or other substances such as for instance blood or tissue elements in the prosthesis 1 can be prevented. This in turn guarantees a safe, secure connection of the socket part 2 with the anchoring part 3.

On the side opposite the (not further designated) entering side for the pins 5, the guides 8 present outlet openings 9, through which dirt and substances such as blood and tissue elements can flow out or be drawn out.

For a better anchoring of the guides 9 in a bone, circular grooves 10 or similar devices may be provided around its outer side.

The connecting device 4 preferably provided in relation to each pin 5 or to each guide 8 comprises a first portion 11 implemented as a recess, preferably as an annular groove in the pins 5, and a second portion 12 provided as a thickening, of a preferably ring-shaped type, in the guides 8.

Figure 2:
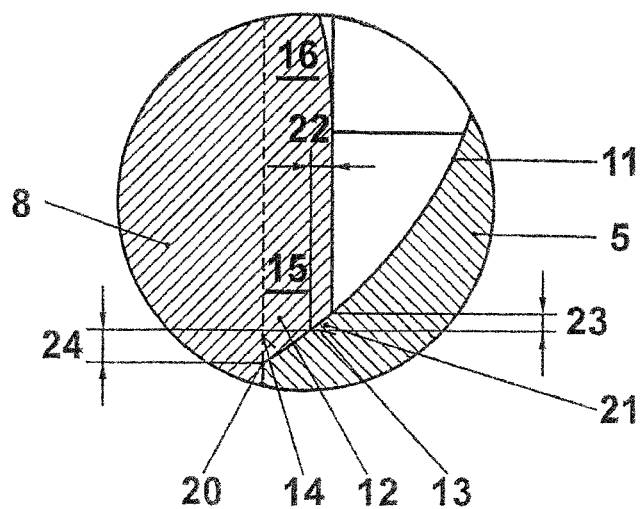
FIG. 2: an enlarged representation of a part of the preferred example of embodiment of the prosthesis according to the invention shown in FIG. 1, and FIG. 3: a cross-sectional representation of a preferred form of embodiment a prosthesis according to the invention, fitted with fastening means.

FIG. 2 shows an enlarged cutaway portion of the prosthesis, which illustrates the connection between the first portion 11 and the second portion 12 of the connecting device 4. The second portion 12 radially projects into the guide 8, where the edge 13 of the second portion 12 that is turned toward the outlet opening 9 of the guide 8 is preferably set at a distance and at an essentially right or at least steep angle from the inner side 14 of the guide. In a vertical or axial direction as seen by the observer, the second portion 12 preferably runs in a direction from the edge 13 toward the socket part 2, in a first stretch 15 parallel to the inner side of the guide 8 and tapers off in a second stretch 16 that follows the first stretch 15 in a vertical or axial direction, until changing over into the inner side 14 of the guide 8.

The anchoring device 3 has a bearing surface 17 that is preferably conformed so that the socket part 3 can be rested on the bearing surface 17 in a planar manner. This advantageously allows achieving a precise seat of the socket part 2 on the anchoring part 3. At the connecting or coupling point, the curving radii of the socket part 3 and the bearing surface 17 are preferably identical, which allows achieving a good contact fit.

The first portion 11 of the connecting device 4 is set up at a distance 18 to the socket part 2 where the distance 18 between the centre of the lower side 19 of the socket part 2 and the extremity 20 turned toward the outlet opening 9 of the first portion 11 and preferably conformed as a groove, preferably amounts to a length of 3 millimeter to 12 millimeter, preferably of 4 mm. The unspecified distance between the bearing surface 17 and the edge 13 of the second portion 12 essentially corresponds to the distance 18.

Because the guide 8 and therefore also the second portion 12 of the connecting device 4 are made of metal and the pin 5 is made of a plastic material, especially polyethylene, when connecting the first portion 11 to the second portion 12, or when connecting the pin 5 to the guide 8, there occurs a deformation of the pin 5, which is induced by the fact that the edge 21 of the second portion 12, which is set at a distance from the inner side 14 of the guide 8 and turned toward the outlet opening 9, presses into the pin 5, thus deforming the same. The radial pressing-in depth 22 for the example of embodiment represented in the FIGS. 1 and 2 amounts to about 0.05 millimeter. The vertical or the axial pressing-in depth 23 for the example of embodiment shown in the FIGS. 1 and 2 amounts to about 0.04 millimeter. The intrusion of the edge 21 of the second portion 12 into the pin 5 prevents the second portion 12 from extending up to the extremity of the first portion 11 that is turned toward the outlet opening 9. Consequently, in the example of embodiment shown, the distance from the bearing surface 17 to the rim 13 of the second portion 12 is smaller, by a difference 24 of about 0.07 millimeters, than the distance 18 from the lower side 19 of the socket part 2 to the lower rim 20 of the first portion 11.

In the example of embodiment shown in the FIGS. 1 and 2, at the point of the first stretch 15 of the second portion 12 of the locking device 4 conformed as a thickening, the guide 8 preferably has an inner diameter of 6.82 millimeter, where the inner diameter of the guide 8, without considering the thickening, preferably amounts to 7 millimeter and the width of the thickening to 0.18 millimeter. At the point of the first portion 11 executed as an opening, the pin 5 preferably has an outer diameter of 6.70 millimeter, where without considering the opening, the outer diameter of the pin 5 preferably amounts to 7 millimeter and the width of the opening 0.3 millimeter. Without considering the thickening 12, the width of the thickening 12 preferably amounts to about five percent of the inner diameter of the guide 8, and without considering the opening 11, the width of the opening 11 amounts to about five percent of the outer diameter of the pin 5. The connecting device 4 preferably has a diameter of 3-9 millimeter, in particular of 6-7 millimeter.

The measurements given in reference to the example of embodiment shown in the FIGS. 1 and 2 allow a secure connection between the socket part 2 and the anchoring part 3 to be made by applying smaller pressing-in forces, while at the same time maintaining the necessary pressing-on forces to release the secure connection.

Figure 3:
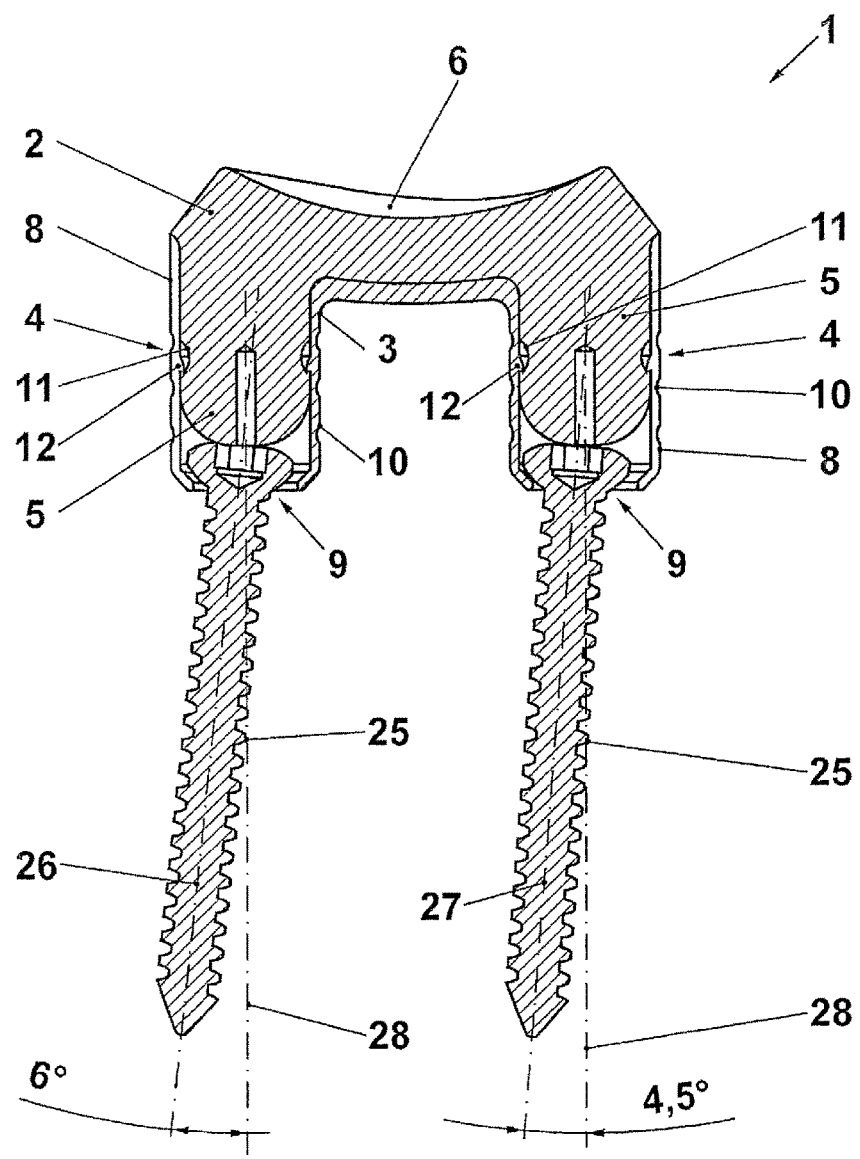

FIG. 3 shows a cross-sectional view of prosthesis 1 as shown in FIG. 1, wherein additionally fastening means 25 passing through the outlet openings 9, especially screws, are provided to fasten the anchoring part 3 in a bone. The axes 26, 27 of the fastening means preferably do not run parallel to the axes 28 of the pins 5. This allows achieving a better anchoring action. The inclination of the axes 26, 27 of the fastening means 25 with respect to the axes 28 of the pins 5 preferably amounts to a value between 4.5 and 6 degrees. A particularly good supporting action in bones can be achieved if the inclination of the axes 26, 27 of the fastening means 25 with respect to the axes 28 of the pins 5 is of a different size. For instance, the inclination of the axis 26 of a first fastening means 25 with respect to the axis 28 of a first pin 5 can be of 6 degrees and the inclination of the axis 27 of a second fastening means 25 with respect to the axis 28 of a second pin 5 can be of 4.5 degrees.

For an implantation or for implanting the prosthesis 1 in a bone, the guides 8 are inserted into the bones in a first phase. This can for instance occur by threading-in the screws 25 and/or applying a force, for instance by a hammer. In a further step, the socket part 2 is connected with the anchoring part 3 by inserting the pins 5 into the guides 8. The pins 5 are inserted into the guides 8 until a secure connection between the socket part 2 or the pins 5 and the anchoring part 3 or the guides 8 has been established. When inserting the pins into the guides 8, they are drawn over the respective thickenings 12 of the connecting devices 4. On this occasion the thickening 12 click or snap into the openings 11 and thus create a secure, meaning non easily releasable connection between the pins 5 and the guides 8 and therefore between the socket part 2 and the anchoring part 3. Such an assembling of the socket part 2 and the anchoring part 3 can of course also be done outside a human or animal body.

The thickening 12 that has been clicked or snapped into the opening 11 prevents the pins 5 from being able to simply slip out of them again. Should the thickening 12 nevertheless, for instance by a swinging motion, be detached from the opening 11, the pins 5 will advantageously still be left inside the guides 8 and be held by these, meaning that the connection of the socket part 2 with the anchoring part 3 is not completely released and remains repairable. A renewed secure connection can be achieved in a simple manner by pressing the socket part 2 and the pins 5 in a direction toward the outlet openings 9 until the thickenings 12 are again snapping into the openings 11.

While preferred embodiments of the invention have been described in the present application, it is to be clearly pointed out that the invention is not limited to these and can, within the range of the following claims, also be embodied in other ways.

The invention claimed is:

1. A prosthesis, comprising:
a socket part receiving a joint head on a pan thereof, the socket part including a plurality of pins extending away from a side of the socket part opposite the pan so that, when inserted into a target portion of bone, the socket part is non-rotatably secured thereto, each of the pins including a locking feature on an outer surface thereof; and
an anchoring part which, when implanted, anchors the prosthesis in a bone, the anchoring part including a plurality of guides formed to receive the pins therein to couple the socket part to the anchoring part in an essentially tilt-proof manner, each of the guides including a locking structure engaging a corresponding one of the locking features, the locking structure projecting into the respective guide, the guides having a first length and the pins having a second length less than the first length so that a distal portion of a first one of the guides receives a portion of a first fastening component that extends past a distal end of the first guide.

2. The prosthesis according to claim 1, wherein the prosthesis is a shoulder prosthesis.

3. The prosthesis according to claim 1, wherein the socket part and the pins are implemented in a single piece.

4. The prosthesis according to claim 1, wherein the guides and the pins are essentially cylindrical, an inner diameter of the guides essentially corresponding to an outer diameter of the pins.

5. The prosthesis according to claim 1, wherein the locking features and the locking structures are snap-in devices.

6. The prosthesis according to claim 1, wherein the distance from the socket part to the connecting device amounts to between 3 mm and 12 mm.

7. The prosthesis according to claim 1, wherein the distance from the socket part to the connecting device is to 4 mm.

8. The prosthesis according to claim 1, wherein the locking feature is conformed as an opening.

9. The prosthesis according to claim 8, wherein the opening includes rims that present a chamfer.

10. The prosthesis according to claim 1, wherein the locking feature is conformed as an essentially annular groove.

11. The prosthesis according to claim 1, wherein the locking structure is formed as a thickening.

12. The prosthesis according to claim 1, wherein the locking structure is formed as an essentially ring-shaped bulge.

13. The prosthesis according to claim 12, wherein the guide has an inner diameter of between 3 mm and 9 mm.

14. The prosthesis according to claim 12, wherein the guide has an inner diameter of 7 mm.

15. The prosthesis according to claim 1, wherein on a side turned away from an inlet side, the guides have an outlet opening.

16. The prosthesis according to claim 15,
wherein the first fastening component fastens the anchoring part in a bone.

17. The prosthesis according to claim 16, wherein the first fastening component includes a screw.

18. The prosthesis according to claim 1, wherein the anchoring part has a bearing surface fitted with an opening to insert the pins into the guides.

19. The prosthesis according to claim 18, wherein the bearing surface is formed so that the socket part is applied to the bearing surface in a planar manner.

20. The prosthesis according to claim 18, wherein the distance from the bearing surface to the connecting device is between 3 mm and 12 mm.

21. The prosthesis according to claim 18, wherein the distance from the bearing surface to the connecting device is to 4 mm.

22. The prosthesis according to claim 1, wherein at least one of the socket part and the pins is made of a plastic material.

23. The prosthesis according to claim 1, wherein at least one of the socket part and the pins is made of polyethylene.

24. The prosthesis according to claim 1, wherein the anchoring part is made of metal.

25. The prosthesis according to claim 1, wherein the pins and the guides are parallel to one another.

26. The prosthesis according to claim 1, wherein a distal portion of a second one of the guides receives a portion of a second fastening component that extends past a distal end of the second guide.

27. A method for assembling a prosthesis, the prosthesis including a socket part, an anchoring part and a locking arrangement, comprising:
inserting a plurality of pins extending away from a side of the socket part opposite a pan in a plurality of guides of the anchoring part, so that, when inserted into a target portion of bone, the socket part is non-rotatably secured thereto, each of the pins including a locking feature on an outer surface thereof; and
wherein the guides have a shape to receive the pins therein to couple the socket part to the anchoring part in an essentially tilt-proof manner, each of the guides including a locking structure engaging a corresponding one of the locking features, the locking structure projecting into the respective guide, the guides having a first length and the pins having a second length less than the first length so that a distal portion of a first one of the guides receives a portion of a first fastening component that extends past a distal end of the first guide.

* * * * *